United States Patent [19]
Gold et al.

[11] Patent Number: 5,567,588
[45] Date of Patent: * Oct. 22, 1996

[54] SYSTEMATIC EVOLUTION OF LIGANDS BY EXPONENTIAL ENRICHMENT: SOLUTION SELEX

[75] Inventors: Larry Gold; Steven Ringquist, both of Boulder, Colo.

[73] Assignee: University Research Corporation, Boulder, Colo.

[ * ] Notice: The term of this patent shall not extend beyond the expiration date of Pat. No. 5,270,163.

[21] Appl. No.: 461,069

[22] Filed: Jun. 5, 1995

Related U.S. Application Data

[63] Continuation of Ser. No. 143,564, Oct. 25, 1993, and a continuation-in-part of Ser. No. 714,131, Jun. 10, 1991, Pat. No. 5,475,096, and Ser. No. 931,473, Aug. 17, 1992, Pat. No. 5,270,163, and Ser. No. 536,428, Jun. 11, 1990, abandoned.

[51] Int. Cl.$^6$ .............................. C12P 19/34; C12Q 1/68
[52] U.S. Cl. .............................. 435/6; 435/91.2; 935/77; 935/78
[58] Field of Search .............................. 435/6, 91.2, 77, 435/78

[56] References Cited

FOREIGN PATENT DOCUMENTS 2183661A  6/1987  United Kingdom.
WO89/06694  7/1989  WIPO.

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Aigen et al. (1991) Methods Enzymol. 208:433.
Baron et al. (1993) Proc. Natl. Acad. Sci. USA 90:4181.
Hartz et al. (1988) Methods Enzymol. 164:419.
Hockensmith et al. (1991) Methods Enzymol. 208:211.
Igloi (1988) Biochemistry 27:3842.

(List continued on next page.)

*Primary Examiner*—Stephanie W. Zitomer
*Attorney, Agent, or Firm*—Swanson & Bartschun LLC

[57] ABSTRACT

Described herein are methods for improved partitioning between high and low affinity nucleic acid ligands identified through the SELEX method, termed solution SELEX. The solution SELEX method achieves partitioning between high and low affinity nucleic acid-target complexes through a number of methods, including (1) primer extension inhibition which results in differentiable cDNA products. Primer extension inhibition is achieved with the use of nucleic acid polymerases, including DNA or RNA polymerases, reverse transcriptase, and Qβ-replicase; (2) exonuclease hydrolysis inhibition which results in only the highest affinity ligands amplifying during PCR. This is achieved with the use of any 3'→5' double-stranded exonuclease; (3) linear to circle formation to generate molecules amplifiable during PCR; or (4) PCR amplification of single-stranded nucleic acids. A central theme of the method of the present invention is that the nucleic acid candidate mixture is screened in solution and results in preferential amplification of the highest affinity RNA ligand or catalytic RNA.

10 Claims, 7 Drawing Sheets

OTHER PUBLICATIONS

Ringquist et al. (1993) Biochemistry in press.
Sasse–Dwight et al. (1991) Methods Enzymol. 208:146.
Tuerk et al., Science 249:505–510 (3 Aug. 1990).
Beandry & Joyce, Science 257:635–641 (31 Jul. 1992).
Bock et al., Nature 355:564–566 (6 Feb. 1992).
Stein et al., Science 261:1004–1112 (20 Aug. 1993).

SYSTEMATIC EVOLUTION OF LIGANDS BY EXPONENTIAL ENRICHMENT: SOLUTION SELEX

This work was supported by grants from the United States Government funded through the National Institutes of Health. The U.S. Government has certain rights in this invention.

This application is a continuation of application Ser. No. 08/143,564 filed on Oct. 25, 1993 which is a Continuation-in-Part of U.S. patent application Ser. No. 07/714,131 filed Jun. 10, 1991, issued as U.S. Pat. No. 5,475,096, entitled Nucleic Acid Ligands, and U.S. patent application Ser. No. 07/931,473, filed Aug. 17, 1992, issued as U.S. Pat. No. 5,270,163 entitled Nucleic Acid Ligands, and U.S. patent application Ser. No. 07/536,428, filed Jun. 11, 1990, now abandoned, entitled Systematic Evolution of Ligands by Exponential Enrichment.

FIELD OF THE INVENTION

The method of the present invention relates to a method for selecting a nucleic acid ligand that specifically binds any desired target molecule. The basic method is termed SELEX, an acronym for Systematic Evolution of Ligands by EXponential enrichment. The SELEX method herein described, termed Solution SELEX, allows more efficient partitioning between oligonucleotides having high and low affinity for a target molecule. The high affinity nucleic acid products of SELEX are useful for any purpose to which a binding reaction may be put, for example in assay methods, diagnostic procedures, cell sorting, as inhibitors of target molecule function, as therapeutic agents, as probes, as sequestering agents and the like.

BACKGROUND OF THE INVENTION

The SELEX method (hereinafter termed SELEX), described in U.S. patent application Ser. No. 07/536,428, filed Jun. 11, 1990, entitled Systematic Evolution of Ligands By Exponential Enrichment, U.S. patent application Ser. No. 07/714,131, filed Jun. 10, 1991, entitled Nucleic Acid Ligands, and U.S. patent application Ser. No. 07/931,473, filed Aug. 17, 1992, entitled Nucleic Acid Ligands, all of which are herein specifically incorporated by reference, provides a class of products which are nucleic acid molecules, each having a unique sequence, each of which has the property of binding specifically to a desired target compound or molecule. Each nucleic acid molecule is a specific ligand of a given target compound or molecule. SELEX is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets.

The SELEX method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by theory, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection, partition and amplification are repeated until a desired goal is achieved. In the most general case, selection/partition/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/partition/amplification iterations.

Current partitioning methods typically used in SELEX rely on a partitioning matrix. High affinity oligonucleotides may be separated in a chromatographic-type process, by binding to nitrocellulose filters, liquid-liquid partition, filtration gel retardation, and density gradient centrifugation.

BRIEF SUMMARY OF THE INVENTION

The method of the present invention, termed solution SELEX, presents several improved methods for partitioning between ligands having high and low affinity nucleic acid-target complexes is achieved in solution and without, or prior to, use of a partitioning matrix. Generally, a central theme of the method of solution SELEX is that the nucleic acid candidate mixture is treated in solution and results in preferential amplification during PCR of the highest affinity nucleic acid ligands or catalytic RNAs. The solution SELEX method achieves partitioning between high and low affinity nucleic acid-target complexes through a number of methods, including (1) Primer extension inhibition which results in differentiable cDNA products such that the highest affinity ligands may be selectively amplified during PCR. Primer extension inhibition is achieved with the use of nucleic acid polymerases, including DNA or RNA polymerases, reverse transcriptase, and Qβ-replicase. (2) Exonuclease hydrolysis inhibition which also results in only the highest affinity ligands amplifying during PCR. This is achieved with the use of any 3'→5' double-stranded exonuclease. (3) Linear to circle formation to generate differentiable cDNA molecules resulting in amplification of only the highest affinity ligands during PCR.

In one embodiment of the solution SELEX method, synthesis of cDNAs corresponding to low affinity oligonucleotides are preferentially blocked and thus rendered non-amplifiable by PCR. In another embodiment, low affinity oligonucleotides are preferentially removed by affinity column chromatography prior to PCR amplification. Alternatively, high affinity oligonucleotides may be preferentially removed by affinity column chromatography. In yet another embodiment of the SELEX method, cDNAs corresponding to high affinity oligonucleotides are preferentially rendered resistant to nuclease enzyme digestion. In a further embodiment, cDNAs corresponding to low affinity oligonucleotides are rendered preferentially enzymatically or chemically degradable.

Solution SELEX is an improvement over prior art partitioning schemes. With the method of the present invention, partitioning is achieved without inadvertently also selecting ligands that only have affinity for the partitioning matrix, the speed and accuracy of partitioning is increased, and the procedure may be readily automated.

Other methods of achieving improved partitioning between high and low affinity oligonucleotides in the SELEX process will become apparent to one skilled in the art from the present disclosure.

DETAILED DESCRIPTION OF THE INVENTION

Figure 1:
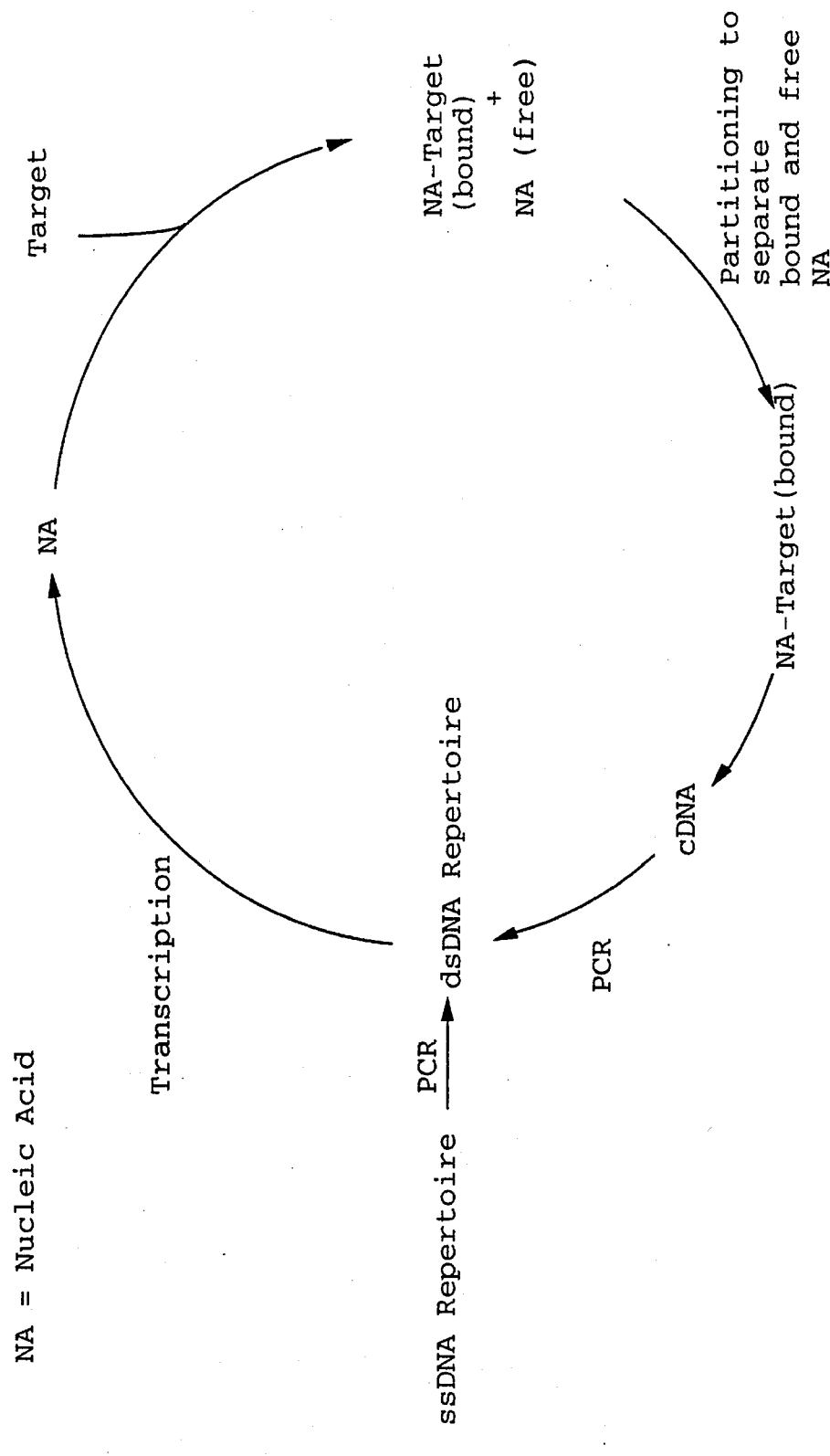
FIG. 1 illustrates the cyclical relationship between SELEX steps. A single-stranded nucleic acid repertoire of candidate oligonucleotides is generated by established procedures on a nucleic acid synthesizer, and is amplified by PCR to generate a population of double-stranded DNA molecules. Candidate DNA or RNA molecules are generated through asymmetric PCR or transcription, respectively, purified, and allowed to complex with a target molecule. This is followed by partitioning of bound and unbound nucleic acids, synthesis of cDNA, and PCR amplification to generate double-stranded DNA.

This application presents a method for improved partitioning of nucleic acid ligands identified through the SELEX method. The SELEX method is described in detail in U.S. patent application Ser. No. 07/714,131 filed Jun. 10, 1991 entitled Nucleic Acid Ligands and Ser. No. 07/536,428 filed Jun. 11, 1990 entitled Systematic Evolution of Ligands by EXponential Enrichment. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the potential of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–10%) is retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

Partitioning means any process whereby ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art. Nucleic acid-protein pairs can be bound to nitrocellulose filters while unbound nucleic acids are not. Columns which specifically retain nucleic acid-target complexes can be used for partitioning. For example, oligonucleotides able to associate with a target molecule bound on a column allow use of column chromatography for separating and isolating the highest affinity nucleic acid ligands. Liquid-liquid partitioning can be used as well as filtration gel retardation, and density gradient centrifugation.

The method of the present invention presents several improved methods for partitioning between oligonucleotides having high and low affinity for a target molecule. The method of the present invention has several advantages over prior art methods of partitioning: (1) it allows the isolation of nucleic acid ligands to the target without also isolating nucleic acid ligands to the partitioning matrix; (2) it increases the speed and accuracy by which the oligonucleotide candidate mixture is screened; and (3) the solution SELEX procedure can be accomplished in a single test tube, thereby allowing the partitioning step to be automated.

The materials and techniques required by the method of the present invention are commonly used in molecular biology laboratories. They include the polymerase chain reaction (PCR), RNA or DNA transcription, second strand DNA synthesis, and nuclease digestion. In practice, the techniques are related to one another in a cyclic manner as illustrated in FIG. 1.

In the SELEX method, described by Tuerk and Gold (1990) Science 249:1155 and illustrated in FIG. 1, a single-stranded nucleic acid candidate mixture is generated by established procedures on a nucleic acid synthesizer, and is incubated with dNTP and Klenow fragment to generate a population of double-stranded DNA templates. The double-stranded DNA or the RNA transcribed from them are purified, and contacted with a target molecule. RNA sequences with enhanced affinity to the target molecule form nucleic acid-target complexes. This is followed by partitioning of bound and unbound nucleic acids, and separation of the target molecule from the bound nucleic acids. cDNA is synthesized from the enhanced affinity nucleic acids and double-stranded DNA generated by PCR amplification. The cycle is repeated until the complexity of the candidate mixture has decreased and its affinity as well as specificity to the target has been maximized.

A novel feature of the solution SELEX method is the means by which the bound and free members of the nucleic acid candidate mixture are partitioned. In one embodiment of the method of the present invention, generation of two physically distinct cDNA pools is accomplished by use of primer extension inhibition. One cDNA extension step is added to the basic SELEX protocol between steps 2 and 3 above, which allows the generation of two physically distinct cDNA pools—one having high affinity for the target and one having low affinity for the target—which are easily distinguished and separated from each other. Primer extension inhibition analysis is a common technique for examining site-bound proteins complexed to nucleic acids (Hartz et al. (1988) Methods Enzymol. 164:419), and relies on the ability of high affinity complexes to inhibit cDNA synthesis. Examples of protein-nucleic acid interactions studied by primer extension inhibition include ribosome binding to the mRNA ribosome-binding site (Hartz et al. (1988) Meth. Enzym. 164:419) as well as binding of the unique *E. coli* translation factor, SELB protein, to the mRNA selenocysteine insertion sequence (Baron et al. (1993) Proc. Natl. Acad. Sci. U.S.A. 90:4181).

Figure 2:
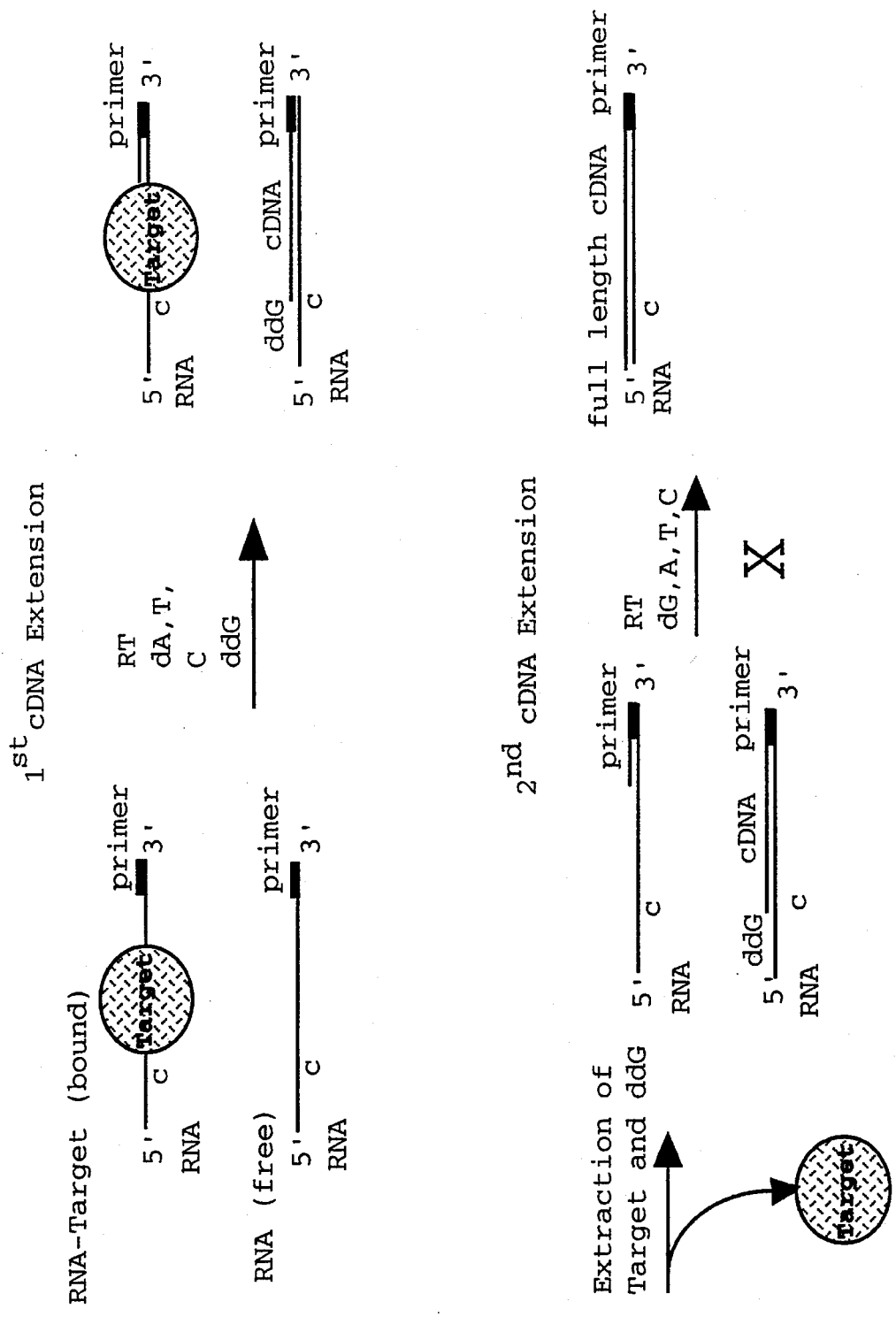
FIG. 2 illustrates one embodiment of the solution SELEX method in which primer extension inhibition is used to create differentiable cDNA pools—an amplifiable high affinity oligonucleotide cDNA pool and a non-amplifiable low affinity oligonucleotide cDNA pool. In this embodiment, the first cDNA extension is performed in the presence of chain terminating nucleotides such as ddG. After removal of the target molecule and dideoxynucleotides, the second cDNA extension is conducted in the presence of four dNTPs. Full-length cDNA is preferentially synthesized from the high affinity oligonucleotides and therefore, the high affinity cDNA pool is amplified in the subsequent PCR step.
Figure 3:
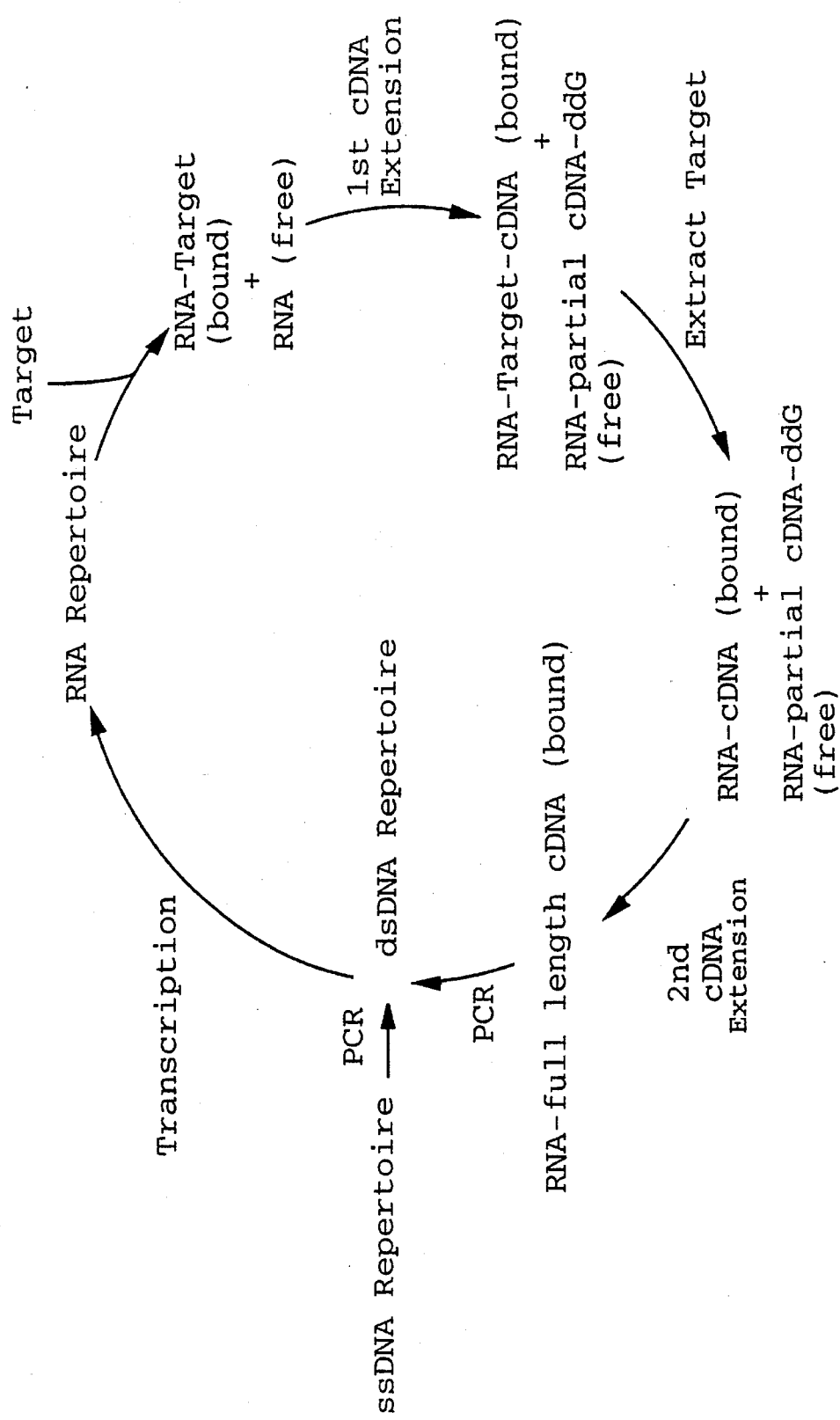
FIG. 3 illustrates the cyclic solution SELEX process for the embodiment shown in FIG. 2.

In one embodiment of the solution SELEX scheme, the first cDNA extension is performed in the presence of chain terminating nucleotide triphosphates. Under these conditions, oligonucleotides with low affinity for the target which form fast dissociating complexes with the target are converted into truncated cDNAs with a 3'-end terminated with a nonextendable nucleotide. The truncated cDNA chain is unable to anneal to the PCR primers, and therefore, is non-amplifiable. In contrast, tight complexes formed between high affinity oligonucleotides and the target molecule, characterized by slow dissociation rates, inhibit cDNA extension. The chain terminators are not incorporated into the nascent cDNA chain synthesized from the high affinity oligonucleotide because cDNA synthesis is blocked by the tightly bound target molecule. Full length cDNA from the high affinity complexes are obtained during a second round of cDNA extension in which the target and chain terminators have been removed from the system. Thus, weak affinity complexes are converted into truncated cDNA lacking the primer annealing site while tight complexes are converted into full length cDNA and are amplified by PCR (FIGS. 2 and 3). The stringency of this method is easily modified by varying the molar ratio of chain terminators and dNTPs or the concentration of the polymerase, as primer extension inhibition is sensitive to polymerase concentration (Ringquist et al. (1993) Biochemistry in press). As used in the present disclosure, the term "stringency" refers to the amount of free RNA that will be converted into PCR product.

Therefore, one crucial feature of the invention is its ability to partition strong and weak affinity complexes into amplifiable and non-amplifiable nucleic acid pools without requiring a partitioning matrix. It is the unique properties of these cDNA pools that allow selective amplification of the high affinity ligand.

The target molecule can be a protein (either nucleic acid or non-nucleic acid binding protein), nucleic acid, a small molecule or a metal ion. The solution SELEX method allows resolution of enantiomers as well as the isolation of new catalytic nucleic acids.

Primer extension inhibition may be achieved with the use of any of a number of nucleic acid polymerases, including DNA or RNA polymerases, reverse transcriptase, and Qβ-replicase.

The candidate mixture of nucleic acids includes any nucleic acid or nucleic acid derivative, from which a complementary strand can be synthesized.

Prior art partitioning included use of nitrocellulose or an affinity column. One disadvantage of the prior art partitioning was the phenomenon of matrix binders in which nucleic acids that specifically bind the partitioning matrix are selected along with those that specifically bind the target. Thus, one advantage of the method of the present invention is that it overcomes unwanted selective pressure originating with use of a partitioning matrix by only using such matrixes after nucleic acids with high affinity for the target have been partitioned in solution and amplified. Moreover, the ability to partition strong and weak affinity complexes during cDNA synthesis, based on the ability of only the strongest complexes to inhibit extension by a polymerase, results in the selection of only the highest affinity nucleic acid ligands. It is estimated that complexes with dissociation constants in the nanomolar or less range will efficiently block cDNA synthesis. The method of the present invention is expected to preferentially screen nucleic acid candidate mixtures for members that bind the target at this limit.

The use of primer extension inhibition allows partitioning of the oligonucleotide candidate mixture into two pools—those oligonucleotides with high target affinity (amplifiable) and those with low target affinity (non-amplifiable). As described above, chain terminators may be used to poison the first extension product, rendering the low affinity cDNAs non-amplifiable.

Figure 4:
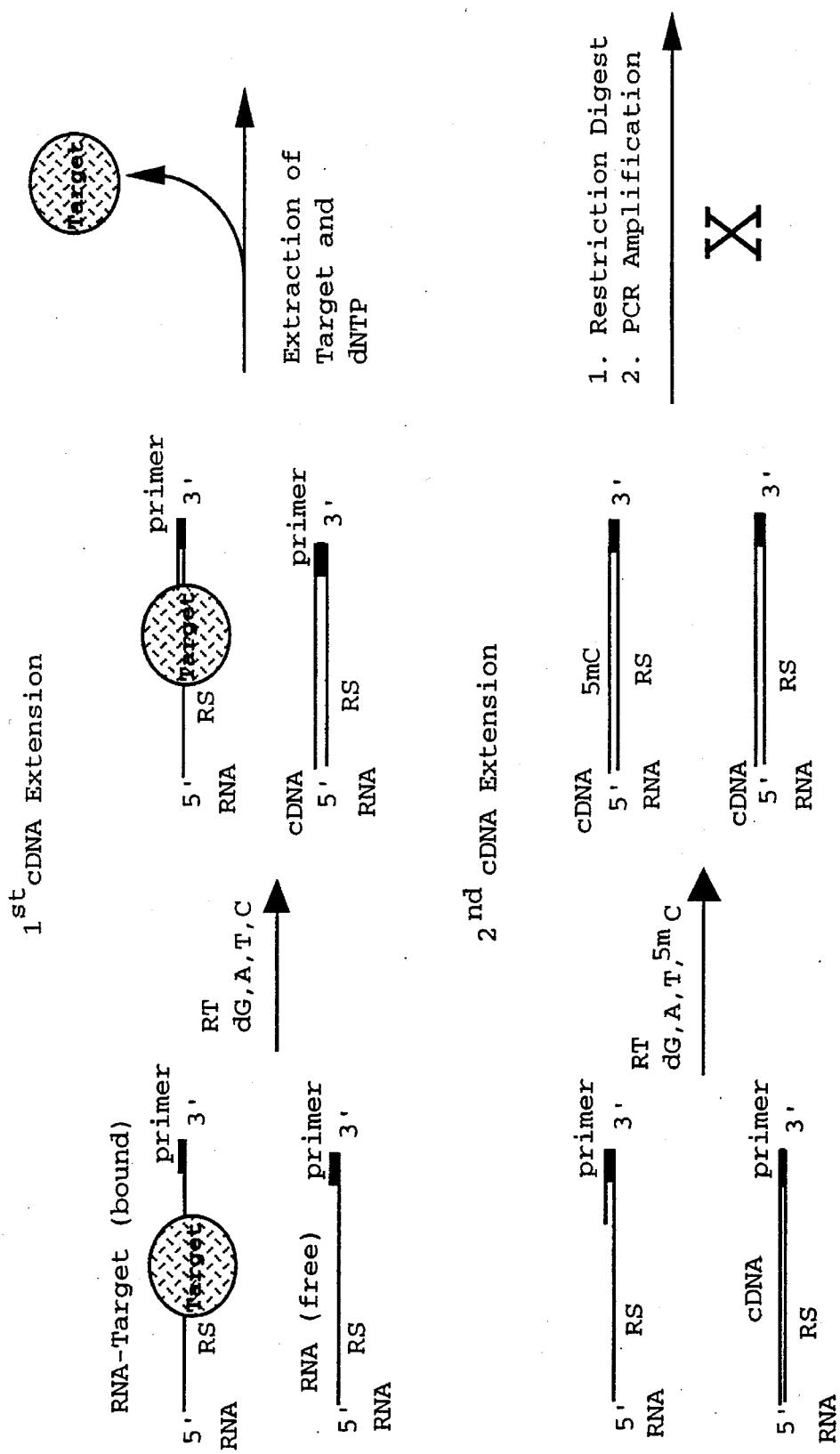
FIG. 4 illustrates one embodiment of the cyclic solution SELEX process wherein partitioning between oligonucleotides having high and low affinity to a target molecule is achieved by restriction enzyme digestion. In this embodiment, the first cDNA extension is conducted with four dNTPs and results in cDNAs corresponding to the low affinity oligonucleotides. The target is then removed and a second cDNA extension is conducted in the presence of modified nucleotides resistant to enzymatic cleavage. The cDNA pools are then incubated with restriction enzyme and only the cDNA pool corresponding to high affinity oligonucleotides is amplifiable in the subsequent PCR step.

In another embodiment of the method of the present invention, restriction enzymes are used to selectively digest the cDNA generated from the low affinity nucleic acids. A number of restriction enzymes have been identified that cleave single-stranded DNA. These enzymes cleave at specific sequences but with varying efficiencies. Partitioning of weak and strong affinity nucleic acids is accomplished by primer extension in the presence of the four dNTPs, followed by removal of the target and a second extension with modified nucleotides that are resistant to enzymatic cleavage. The cDNA pools can then be incubated with the appropriate restriction enzyme and the cDNA synthesized during the first extension cleaved to remove the primer annealing site and yield a non-amplifiable pool. Increased efficiency of cleavage is obtained using a hairpin at the restriction site (RS) to create a localized double-stranded region (FIG. 4).

In another embodiment of method of the present invention, cDNA sequences corresponding to low affinity nucleic acids are rendered selectively degradable by incorporation of modified nucleotide into the first cDNA extension product such that the resulting cDNA is preferentially degraded enzymatically or chemically.

Figure 5:
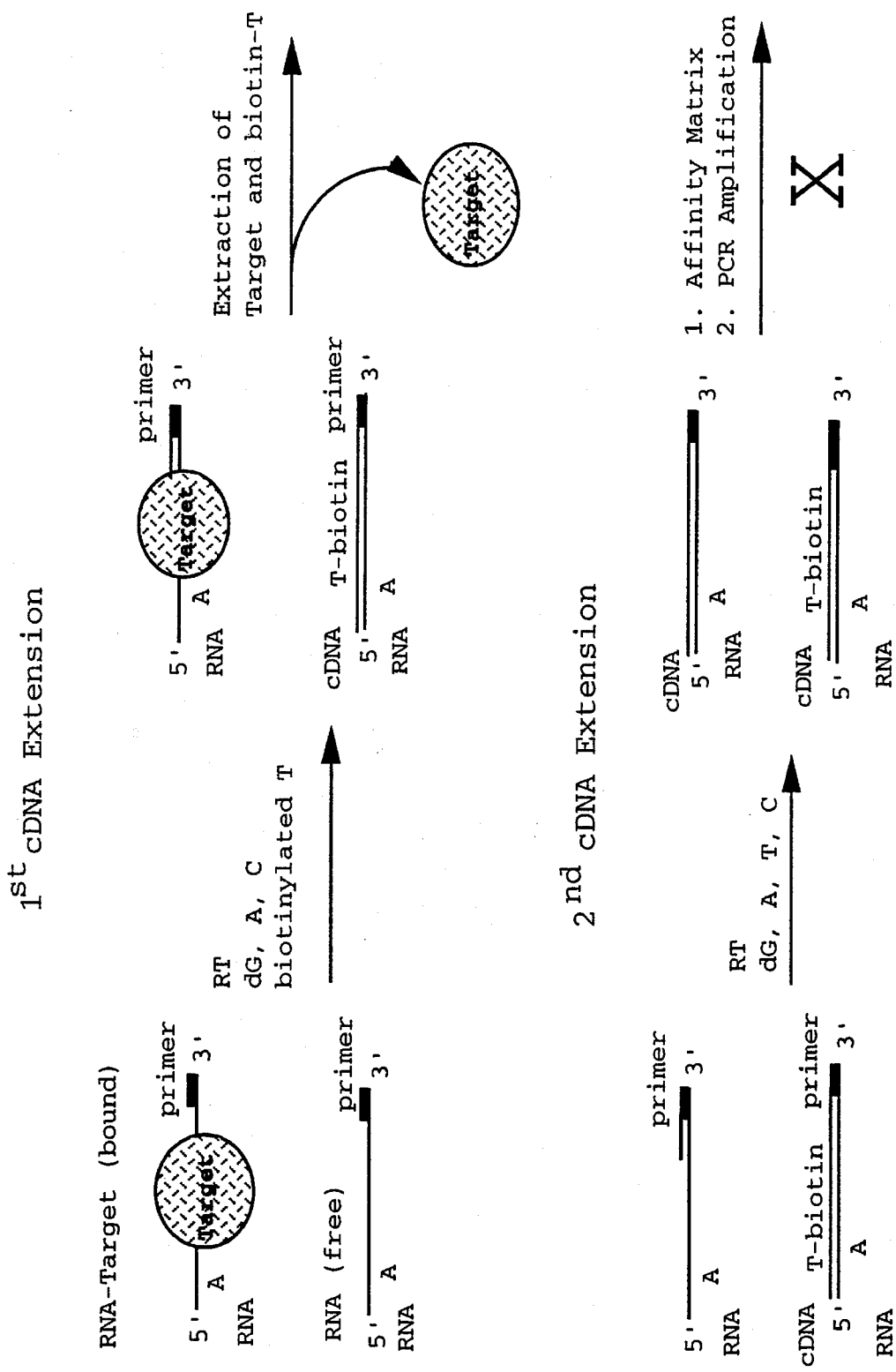
FIG. 5 illustrates one embodiment of the cyclic solution SELEX process wherein partitioning between oligonucleotides having high and low affinity to a target molecule is achieved by affinity chromatography. The first cDNA extension is performed in the presence of a modified nucleotide such as a biotinylated nucleotide, which allows the cDNA pool corresponding to the low-affinity oligonucleotide to be retained on an affinity column.

In another embodiment of the method of the present invention, the first extension product can be removed from the system by an affinity matrix. Alternatively, the matrix could be used to bind the second extension product, e.g., the cDNAs corresponding to high affinity nucleic acids. This strategy relies on the incorporation of modified nucleotides during cDNA synthesis. For instance, the first cDNA extension could be performed in the presence of modified nucleotides (e.g., biotinylated, iodinated, thiolabelled, or any other modified nucleotide) that allow retention on an affinity matrix (FIG. 5). In an alternate embodiment of the method of the present invention, a special sequence can also be incorporated for annealing to an affinity matrix. Thus, first synthesis cDNAs can be retarded on commercially obtainable matrices and separated from second synthesis cDNA, synthesized in the absence of the modified nucleotides and target.

In another embodiment of the invention, exonuclease hydrolysis inhibition is used to generate a pool of high affinity double-stranded nucleic acid ligands.

In yet another embodiment of the invention, the solution SELEX method is used to isolate catalytic nucleic acids.

In another embodiment of the invention, solution SELEX is used to preferentially amplify single-stranded nucleic acids.

In a further embodiment of the invention, the solution SELEX method is automated.

Removal of the target to allow cDNA synthesis from the high affinity nucleic acids can also be accomplished in a variety of ways. For instance, the target can be removed by organic extraction or denatured by temperature, as well as by changes in the electrolyte content of the solvent. In addition, the molecular repertoire of the candidate mixture that can be used with the invention include any from which a second complementary strand can be synthesized. Single-stranded DNA as well as RNA can be used, as can a variety of other modified nucleotides and their derivatives.

The following non-limiting examples illustrate the method of the present invention. Example 1 describes the solution SELEX process wherein partitioning between high and low affinity nucleic acids is achieved by primer extension inhibition. Example 2 illustrates the solution SELEX process wherein partitioning is achieved by restriction enzyme digestion of low affinity RNA. Example 3 describes the solution SELEX process wherein low affinity nucleic acids are separated from high affinity nucleic acids by affinity chromatography. Example 4 describes the isolation of high affinity double-stranded nucleic acid ligands with the use of exonuclease inhibition. Example 5 describes the isolation of catalytic nucleic acids. Example 6 describes an automated solution SELEX method.

EXAMPLE 1

Primer Extension Inhibition Solution SELEX.

Primer extension inhibition relies on the ability of a tightly bound target molecule to inhibit cDNA synthesis of high affinity oligonucleotides and results in formation of an amplifiable cDNA pool corresponding to high affinity oligonucleotides and a non-amplifiable cDNA pool corresponding to low affinity oligonucleotides. Thus, the PCR step of solution SELEX acts as a partitioning screen between two cDNA pools. General protocols for nucleic acid synthesis, primer extension inhibition and PCR are herein provided. Further, N-acryloylamino phenyl mercuric gel electrophoretic conditions for separation of selected nucleic acid ligands is described. The methods of cloning and sequencing nucleic acid ligands is as described by Tuerk and Gold (1990) supra.

RNA synthesis. The RNA candidate mixture was generated by incubating RNA polymerase and DNA templates. The reaction conditions are 8% polyethylene glycol 8000, 5 mM dithiothreitol, 40 mM Tris-HCl (pH 8.0), 12 mM $MgCl_2$, 1 mM spermidine, 0.002% Triton X-100, 2 mM nucleotide triphosphates, and 1 unit/µl RNA polymerase. Reactions are incubated at 37° C. for 2 hours.

The transcription protocol may be used to generate RNAs with modified nucleotides. The transcription reaction may either be primed with a nucleotide triphosphate derivative (to generate a modified 5' end), modified nucleotides may be randomly incorporated into the nascent RNA chain, or oligonucleotides or their derivatives ligated onto the 5' or 3' ends of the RNA product.

Primer Extension Inhibition.

Primer extension inhibition is performed as described by Hartz et al. (1988) supra. Briefly, an oligonucleotide primer is annealed to the 3' end of the oligonucleotides of the candidate mixture by incubating them with a 2-fold molar excess of primer at 65° C. for 3 min in distilled water. The annealing reaction is cooled on ice, followed by the addition of 1/10 volume of 10× concentrated extension buffer (e.g., 10 mM Tris-HCl (pH 7.4), 60 mM $NH_4Cl$, 10 mM Mg-acetate, 6 mM β-mercaptoethanol, and 0.4 mM nucleotide triphosphates). Primer extension is initiated by addition of polymerase and incubation at any of a variety of temperatures ranging between 0°–80° C., and for times ranging from a few seconds to several hours. In one embodiment of the method of the present invention, primer extension is first conducted in the presence of chain terminating nucleotide triphosphates such that low-affinity nucleic acids preferentially incorporate these chain terminators. A second primer extension is then conducted after removing the target from high affinity nucleic acids and removing the chain terminating nucleotide triphosphates.

Polymerase Chain Reaction.

The polymerase chain reaction (PCR) is accomplished by incubating an oligonucleotide template, either single- or double-stranded, with 1 unit/µl thermal stable polymerase in buffer (50 mM KCl, 10 mM Tris-HCl (pH 8.6), 2.5 mM $MgCl_2$, 1.7 mg/ml BSA, 1 mM deoxynucleotide triphosphates, and 1 µM primers). Standard thermal cycles are 95° C. for 30 sec, 55° C. for 30 sec, and 72° C. for 1 min, repeated as necessary. One modification of the PCR protocol generates single-strand DNA by incubating either single- or double-stranded template with a single, elongated primer oligonucleotides and results in an elongated product. PCR preferentially amplifies the oligonucleotides rendered amplifiable in the primer extension steps described above.

(N-Acryloylamino)phenyl mercuric gel electrophoresis.

Polyacrylamide gel electrophoresis using N-acryloylamine phenyl mercury (APM) was performed as described by Igloi (1988) Biochemistry 27:3842. APM was synthesized by mixing 8 ml of acetonitrile to 0.35 g of (p-aminophenyl)mercuric acetate at 0° C., followed by 2 ml of 1.2M $NaHCO_3$. A total of 0.2 ml of acryloyl chloride was then added with vigorous stirring and the reaction incubated, overnight at 4° C. The solid phase was collected by centrifugation and washed with water, dissolved by warming to 50° C. in 8.5 ml of dioxane, followed by filtration to remove undissolved contaminants. APM crystals were formed upon standing at room temperature and the solid was washed again with water and dried under vacuum. APM was stored at 4° C. APM-polyacrylamide gels were prepared by addition of a appropriate aliquot of a 1 mg/ml solution of APM in formamide to a solution containing a given amount of acrylamide, bis(acrylamide), an urea in 0.1M Tris-borate/EDTA (pH 8.3). Polymerization was initiated by addition of 0.5 ml of 1% ammonium persulfate and 7 ul of TEMED per 10 ml of gel solution.

EXAMPLE 2

Enzymatic or Chemical Degradation Solution SELEX.

Enzymes or chemicals may be used to selectively degrade the pool of cDNA corresponding to low-affinity oligonucleotides. In one embodiment of the present invention, restriction enzymes are used to selectively degrade the cDNA pool corresponding to low-affinity oligonucleotides. A number of restriction enzymes have been identified that cleave single-stranded DNA. These enzymes cleave at specific sequences but with varying efficiencies.

Restriction enzyme digestion may be performed with a variety of sequence specific restriction endonucleases. Endonucleases that cleave single-stranded DNA include DdeI, HaeIII, HgaI, HinfI, HinPI, MnII, PstI, and RsaI. These enzymes are used under standard conditions known to those skilled in the field of molecular biology. Double-stranded nucleic acids may also be cleaved using the proper combination of nucleic acid restriction sequences and site specific restriction nucleases.

The basic solution SELEX procedure is followed as described in Example 1. The first cDNA extension is performed in the presence of four dNTPS, followed by removal of the target. The second cDNA extension is performed with modified nucleotides that are resistant to enzymatic cleavage by restriction endonucleases. The mixture of cDNA extension products is incubated with the appropriate restriction enzyme. The product of the first cDNA extension from free nucleic acid is cleaved to remove the primer annealing site, rendering this cDNA pool non-amplifiable by PCR. The efficiency of cleavage by restriction endonucleases may be improved using a hairpin at the restriction site (RS) to create a localized double-stranded region, as shown in FIG. 4.

Alternatively, the first cDNA extension product is rendered selectively degradable by other classes of enzymes by incorporation of modified nucleotides. For example, cDNA corresponding to low affinity ligands may be synthesized with nucleotides sensitive to uracil DNA glycosylase, while cDNA corresponding to high affinity ligands may incorporate resistant nucleotides.

Chemical degradation of cDNA corresponding to low affinity ligands can be accomplished by incorporation of 7-methylguanosine, 5-bromouracil, or 5-iodouracil as described using piperidine or photodegradation (Sasse-Dwight and Gralla (1991) Methods Enzymol. 208:146; Aigen and Gumport (1991) Methods Enzymol. 208:433; Hockensmith et al. (1991) Methods Enzymol. 208:211).

EXAMPLE 3

Solution SELEX Followed by Affinity Chromatography.

Selective removal of either the first or second cDNA extension products may be achieved through affinity chromatography. Removal of the first cDNA extension product preferentially removes the cDNA pool corresponding to free or low-affinity nucleic acids. Removal of the second cDNA extension product preferentially retains cDNA corresponding to the high-affinity ligand. This strategy relies on the incorporation of modified nucleotides during cDNA synthesis.

Selective Removal of First Extension Product.

Following the basic solution SELEX protocol outlined in Example 1, the first cDNA extension is performed in the presence of modified nucleotides (e.g., biotinylated, iodinated, thiolabelled, or any other modified nucleotide) that allow retention of the first cDNA pool on an affinity matrix (FIG. 5). The target is then removed and the second cDNA extension performed in the presence of non-modified nucleotides. The cDNAs that have incorporated the modified nucleotides may be removed by affinity chromatography using a column containing the corresponding affinity ligand. The cDNA pool corresponding to nucleic acids with high affinity for the target remain and are then amplified by PCR.
Selective Removal of the Second Extension Product.

Following the basic protocol outlined in Example 1, the first cDNA extension is performed in the presence of four dNTPs, and the second cDNA extension is performed in the presence of modified nucleotides (e.g., biotinylated, iodinated, thiolabelled, or any other modified nucleotide) that allow retention of the second cDNA pool on an affinity matrix as described above.
Incorporation of Specific Sequences for Annealing to An Affinity Matrix.

In an alternate embodiment of the method of the present invention, a special sequence can also be selectively incorporated for annealing to an affinity matrix. Thus, either first or second synthesis cDNAs can be retarded and purified on commercially obtainable matrices as desired.

EXAMPLE 4

Exonuclease Inhibition Solution SELEX.

Figure 6:
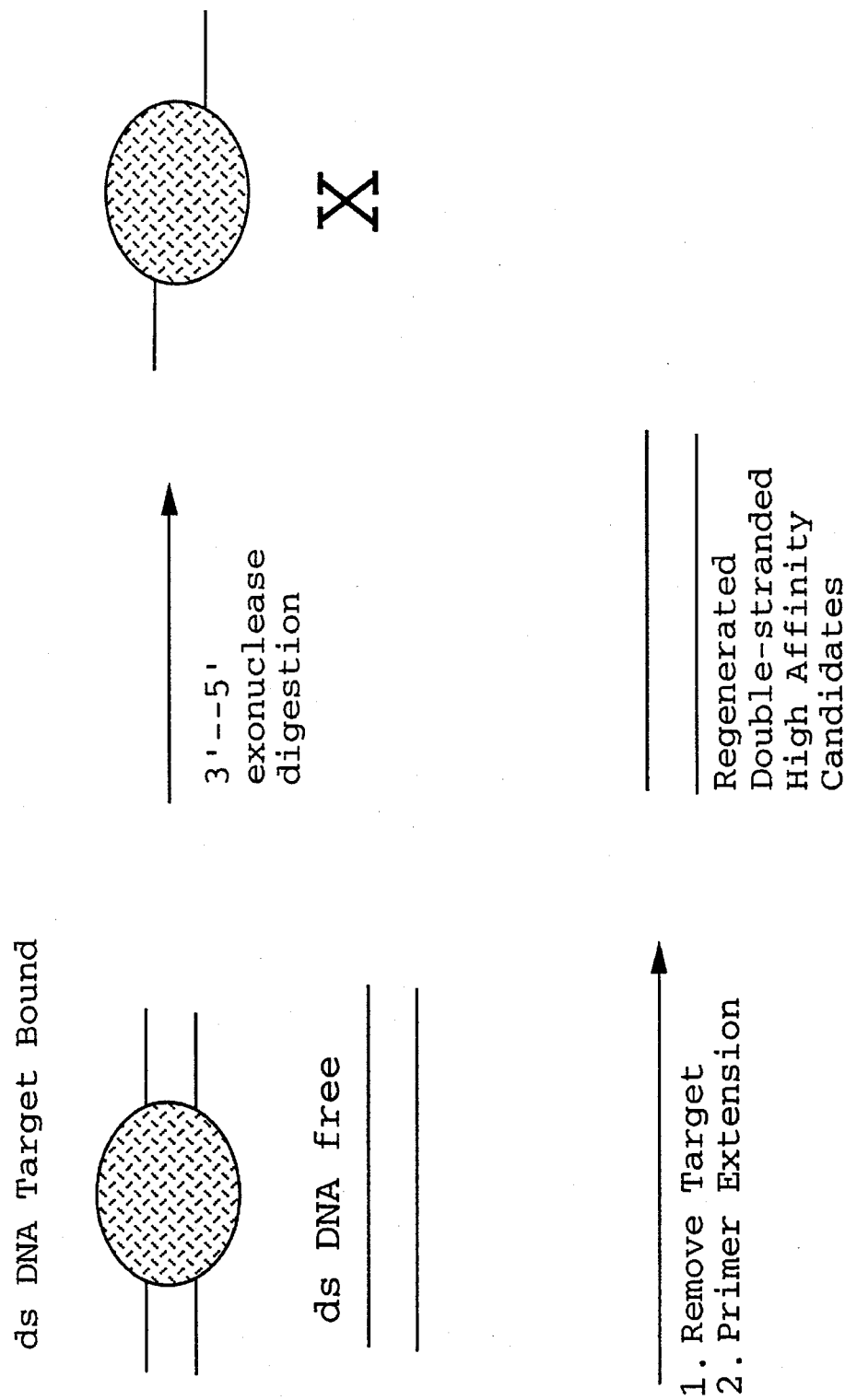
FIG. 6 illustrates one embodiment of the solution SELEX process wherein partitioning between oligonucleotides having high and low affinity to a target molecule is achieved by exonuclease digestion and results in formation of a double-stranded nucleic acid population with high affinity for the target molecule.

Exonuclease inhibition may be used to isolate double-stranded ligands. Double-stranded nucleic acid ligands tightly bound to the target molecule will inhibit exonuclease hydrolysis at the 3' edge of the binding site. This results in a population of nucleic acid molecules resistant to hydrolysis that also contain a long single-stranded 5' overhang and a central base paired region (see FIG. 6). This nucleic acid molecule is a substrate for any polymerase, and incubation with polymerase will generate the double-stranded starting material. This molecule is amplified by PCR. Members of the nucleic acid candidate mixture that are not tightly bound to the target molecule are digested during the initial exonuclease step.

$3' \rightarrow 5'$ hydrolysis of double-stranded nucleic acid is accomplished by incubation with any double-stranded specific $3' \rightarrow 5'$ exonuclease. Exonuclease III specifically hydrolyzes double-stranded DNA $3' \rightarrow 5'$ and is active in a variety of buffers, including 50 mM Tris-HCl (pH 8.0), 5 mM $MgCl_2$, 10 mM β-mercaptoethanol at 37° C.

EXAMPLE 5

Solution SELEX Method for Isolating Catalytic Nucleic Acids.

Solution SELEX may be used to isolate catalytic nucleic acid sequences. This embodiment of the invention takes advantage of a linear to circular transformation to sort non-catalytic nucleic acids from catalytic nucleic acids.

Figure 7:
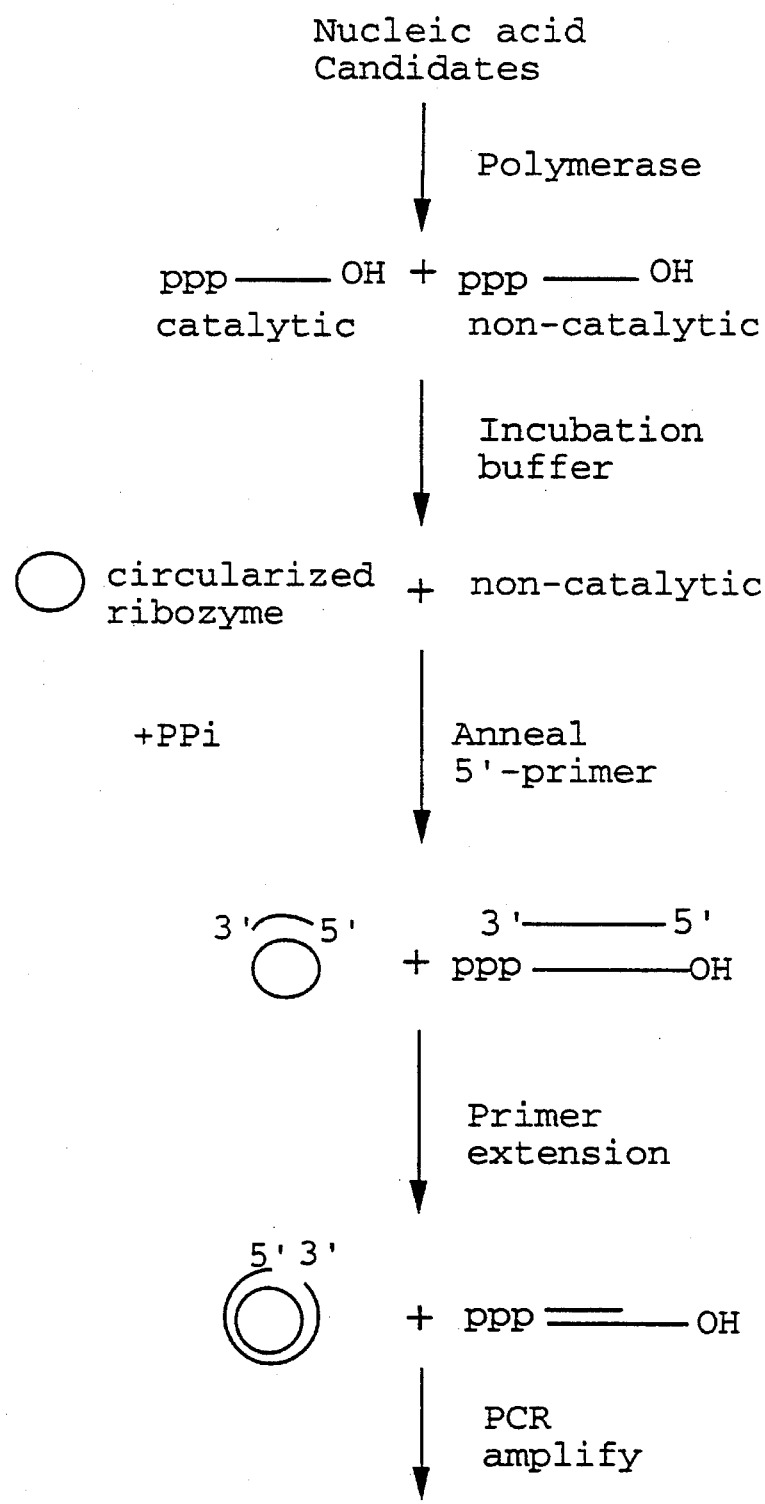
FIG. 7 illustrates one embodiment of the solution SELEX process wherein catalytic nucleic acids are selected and isolated.

As shown in FIG. 7, the PCR step may be exploited to screen the nucleic acid candidate mixture for catalytic members. Catalytic nucleic acids that either self-circularize, or alter their 5' or 3' ends to allow circularization with ligase, will amplify during PCR. The figure illustrates circle formation by catalytic members of the candidate mixture; the non-catalytic oligonucleotide members of the candidate mixture will remain linear. After circularization, the candidate mixture is incubated with a primer that anneals to the extreme 5' end. In this embodiment of the invention, only the circular oligonucleotide members will generate cDNA and be amplified during the PCR step.

This strategy isolates nucleic acids that either directly catalyze self-circularization or that modify their own ends so that the amplifiable form may be generated by incubation with ligase. As shown in FIG. 7, the unusual interaction of the cDNA primer with the 5' end of the oligonucleotides of the candidate mixture permits amplification of only the circular molecules. In a further embodiment of the method of the present invention, this strategy is modified to allow isolation of catalytic nucleic acids that catalyze novel reactions.

EXAMPLE 6

Automation of Solution SELEX.

The automated solution SELEX protocol represents a modification of the technology used in the automated DNA synthesizer. The nucleic acid candidate mixture is attached to a solid support by either the biotin/avidin interaction or a variety of covalent chromatographic techniques (e.g., the condensation of modified nucleotides onto maleimide or citraconic anhydride supports). The bound nucleic acid candidate mixture provides a good substrate for targeting binding, and the column allows use of a single reaction vessel for the SELEX procedure. Primer extension inhibition is used to physically sort low and high affinity ligands. Low affinity nucleic acids may be degraded by incorporation of modified nucleotides during the first cDNA extension step that renders the cDNA degradable as described in Example 2, while high affinity ligands are copied into non-degradable cDNA and amplified by PCR. For additional rounds of solution SELEX, the PCR generated candidate mixture is purified or is transcribed into RNA and reattached to a second solid support, in the same or a new reaction vessel as desired. The process is repeated as necessary.

We claim:

1. A method for identifying nucleic acid ligands from a candidate mixture of nucleic acids, said nucleic acid ligands being a ligand of a given target molecule comprising:

a) contacting said candidate mixture with the target molecule, wherein nucleic acids having increased affinity to the target molecule form nucleic acid-target complexes;

b) partitioning the increased affinity nucleic acids from the remainder of the candidate mixture, said partitioning step resulting in two differentiable nucleic acid pools said nucleic acids in each pool having different relative affinities to said target molecule; and c) amplifying the increased affinity nucleic acids to yield a ligand-enriched mixture of nucleic acids, whereby nucleic acid ligands of the target molecule may be identified.

2. The method of claim 1 wherein said partitioning in step b) comprises:

(i) performing a first primer extension with a nucleic acid polymerase under conditions wherein the increased affinity nucleic acids associated with said nucleic acid-target complexes are not primed;

(ii) removing the target molecule;

(iii) performing a second primer extension with a nucleic acid polymerase under conditions different from step (i), wherein said increased affinity nucleic acids are primed and said two differentiable nucleic acid, pools result from step (i) and step (iii); and (iv) partitioning the increased affinity nucleic acid pool of step (iii) from the remainder of the candidate mixture.

3. The method of claim 2, wherein said nucleic acid polymerase is selected from the group consisting of DNA polymerase, RNA polymerase, reverse transcriptase, and Qβ-replicase.

4. The method of claim 2 wherein said first primer extension is performed in the presence of chain terminating nucleotides and said second primer extension is performed in the absence of chain terminating nucleotides, wherein only the primer extension product from the increased affinity oligonucleotide is amplifiable by a polymerase chain reaction.

5. The method of claim 2 wherein said first primer extension is performed in the presence of unmodified nucleotides, followed by removal of said target, said second primer extension is performed in the presence of modified nucleotides resistant to enzymatic cleavage by single- or double-stranded nucleases, or uracil DNA glycosylase, and the primer extension products are incubated with an appropriate cleaving enzyme, whereby only the primer extension product from the increased affinity oligonuclcotides are amplifiable by a polymerase chain reaction.

6. The method of claim 2 wherein said first primer extension is performed in the presence of modified nucleotides that allow retention of the first primer extension product on an affinity matrix, followed by removal of said target, said second primer extension is performed in the presence of unmodified nucleotides, and the product primed from said first primer extension is removed by retention on an affinity matrix.

7. The method of claim 2 wherein said first primer extension is performed in the presence of modified nucleotides, followed by removal of said target, said second primer extension is performed in the presence of modified nucleotides that allow retention of the second primer extension product on an affinity matrix, and the product of the second primer extension from increased affinity oligonucleotides is removed by retention on an affinity matrix.

8. A method for identifying nucleic acid ligands from a candidate mixture of nucleic acids, said nucleic acid ligands being a ligand of a given target molecule comprising:
   a) contacting said candidate mixture with the given target molecule, wherein nucleic acids having an increased affinity to the target molecule form nucleic acid-target complexes;
   b) partitioning the increased affinity nucleic acids from the remainder of the candidate mixture, said partitioning step comprising:
      (i) performing a first primer extension with a nucleic acid polymerase in the presence of nucleotides sensitive to chemical cleavage;
      (ii) removing the target molecule;
      (iii) performing a second primer extension with a nucleic acid polymerase in the presence of modified nucleotides resistant to chemical cleavage;
      (iv) incubating said first and second primer extension products with a nucleotide cleaving chemical, whereby the extension product of the first primer extension is cleaved; and
   c) amplifying the increased affinity nucleic acids to yield a ligand-enriched mixture of nucleic acids, whereby nucleic acid ligands of the given target molecule may be identified.

9. A method for identifying double-stranded nucleic acid ligands from a candidate mixture of nucleic acids, said double-stranded nucleic acid ligands being a ligand of a given target molecule comprising:
   a) contacting said candidate mixture with the given target molecule, wherein nucleic acids having an increased affinity to the target molecule form nucleic acid-target complexes;
   b) partitioning the increased affinity nucleic acids from the remainder of the candidate mixture, said partitioning step comprising:
      (i) incubating the increased affinity nucleic acids with exonuclease wherein full length double-stranded nucleic acids not forming nucleic acid-target complexes are degraded and the double-stranded nucleic acids forming nucleic acid-target complexes are partially protected from degradation;
      (ii) removing said exonuclease and said target;
      (iii) primer extending said double-stranded nucleic acids with polymerase, wherein the double-stranded nucleic acid ligand-enriched candidate mixture is regenerated from the partially protected nucleic acids; and
   c) amplifying the primer extended double-stranded nucleic acids to yield a ligand-enriched mixture of double-stranded nucleic acids, whereby the double-stranded nucleic acid ligands of the given target molecule may be identified.

10. The method of claim 5 wherein said cleaving enzyme is selected from the group consisting of restriction endonuclease and uracil DNA glycosylase.

* * * * *